United States Patent
Ridihalgh

(10) Patent No.: US 6,713,054 B1
(45) Date of Patent: Mar. 30, 2004

(54) CELLULAR IMMUNOTHERAPY TREATMENT OF PATIENTS AFFLICTED WITH CHRONIC FATIGUE SYNDROME

(75) Inventor: John L. Ridihalgh, Columbus, OH (US)

(73) Assignee: Cira Technologies, Inc., Columbus, OH (US)

( * ) Notice: Subject to any disclaimer, the term of this patent is extended or adjusted under 35 U.S.C. 154(b) by 528 days.

(21) Appl. No.: 09/167,764

(22) Filed: Oct. 7, 1998

(51) Int. Cl.[7] .............................................. A61K 35/00
(52) U.S. Cl. ...................................................... 424/93.1
(58) Field of Search ........................... 424/93.1; 435/325

(56) References Cited

PUBLICATIONS

Levine et al. Am. J. Med., vol. 105, pp. 100S–103S, Sep. 28, 1998.*
Caplan, Can. Med. Assoc. J., vol. 159, pp. 519–520, Sep. 8, 1998.*
Goldberg, Curr. Op. in Rheum., vol. 9, pp. 135–143, Mar. 1997.*
Peakman et al. Clin. Immuno. and Immunopath., vol. 82, pp. 82–91, Jan. 1997.*

* cited by examiner

*Primary Examiner*—Michael Wilson
(74) *Attorney, Agent, or Firm*—Mueller and Smith, LPA

(57) ABSTRACT

Broadly, disclosed is a novel approach to the treatment of chronic fatigue syndrome (CFS) that exploits the effective cellular immune response that is initially generated in CFS individuals. One aspect is a method for preparing cells for treating patients afflicted with CFS, which includes subjecting cytokine-producing cells derived from lymph nodes excised from patients afflicted with CFS to mitogenic stimulation in serum-free media for their expansion. The resulting therapeutic agent for treating patients afflicted with CFS includes in a pharmaceutically-acceptable carrier cytokine-producing having been produced by the step of subjecting cells derived from lymph nodes excised from patients afflicted with CFS to mitogenic stimulation in serum-free media for their expansion. As another aspect of the present invention, disclosed is a method for treating patients afflicted with CFS that includes administering to the patient an effective amount of the therapeutic agent disclosed herein. The invention also is capable of treating individuals afflicted with fibromyalgia syndrome ("FMS"). Finally, the invention further is effective in lowering activated T cell count in individuals.

8 Claims, 6 Drawing Sheets

CELLULAR IMMUNOTHERAPY TREATMENT OF PATIENTS AFFLICTED WITH CHRONIC FATIGUE SYNDROME

CROSS-REFERENCE TO RELATED APPLICATIONS

This application is cross-referenced to commonly-assigned application Ser. No. 08/604,728, filed Feb. 21, 1996, now abandoned the disclosure of which is expressly incorporated herein by reference.

STATEMENT REGARDING FEDERALLY SPONSORED RESEARCH

Not applicable.

BACKGROUND OF THE INVENTION

The present invention relates to chronic fatigue syndrome ("CFS") and more particularly to a novel cellular therapy treatment thereof.

CFS is characterized by debilitating fatigue that is not attributable to known clinical conditions, that has lasted for over 6 months, that has reduced the activity level of a previously healthy person by greater than 50%, and that has been accompanied by flu-like symptoms (e.g., pharyngitis, adenopathy, low-grade fever, myalgia, arthralgia, headache) and neuropsychological manifestations (e.g., difficulty concentrating, exercise intolerance, and sleep disturbances). Klimas, et al., "Chronic Fatigue Syndrome", *Curr. Opin. Inf. Dis.*, 8:145–148 (1995); Buchwald, et al., "Chronic illness characterized by fatigue, neurologic and immunologic disorders and active human herpesvirus 6 type infection", *Ann. Int. Med.*, 116:103–113 (1992); Millon, et al., "A psychological assessment of chronic fatigue syndrome/chronic Epstein-Barr virus patients", *Psychol. Health.*, 3:131–141 (1989); Lutgendorf, et al., "Relationships of cognitive difficulties, depression and illness burden in chronic fatigue syndrome", *J. Chronic Fatigue Syn.*, 1:23–41 (1995); Fukuda, et al., and the International CFS Study Group, "The Chronic Fatigue Syndrome: A comprehensive approach to its definition and study", *Ann. Intern. Med.*, 121:953–959 (1994), Klimas, et al., "Chronic Fatigue Syndrome", *Curr. Opin. Inf. Dis.*, 8:145–148 (1995). CFS frequently is of sudden onset. Possible precipitating events include, for example, infections, psychiatric trauma, and exposure to toxins. Klimas, "Chronic fatigue syndrome and psychoneuroimmunology", In *Stress and Disease Progression: Perspectives in Behavioral Medicine*", Schneiderman, et al., eds., Lawrence Erlbaum, Assoc., Hillsdale, NJ, pp. 121–137 (1992); Chester, et al., "Concurrent sick building syndrome and chronic fatigue syndrome". *Clin. Inf. Dis..*, 18 (suppl. 1):S43–48 (1994): Ablashi, et al., "Viruses and chronic fatigue syndrome: Current status", *J. Chronic Fatigue Syn.*, 1:3–22 (1995).

The definition adopted by the Center for Disease Control and Prevention is set forth in Fukuda, et al., and the International CFS Study Group, "The Chronic Fatigue Syndrome: A comprehensive approach to its definition and study", supra. For further information and articles on CFS, reference is made to the CDC website located at www.cdc.gov/ncicdod/disease.cfs. It should be noted that a related illness closely associated with CFS is fibromyalgia syndrome ("FMS"), because of its substantial symptom overlap with CFS. Further information on FMS can be found from, for example, the Fibromyalia Network at www.fm-netnews.com (Fibromyalgia Network, Tucson, Ariz.). Often, patients presenting with CFS also will be diagnosed with FMS.

Despite the studies reported above and others, both the cause and treatment of CFS and FMS remain beyond the grasp of present-day medicine. The present invention, however, will change these unknowns by providing a treatment for CFS and FMS that has been shown to materially offer hope to those afflicted by this debilitating condition.

BRIEF SUMMARY OF THE INVENTION

The present invention relates to the treatment of CFS and FMS that exploits the effective cellular immune response that is initially generated in CFS individuals. One aspect is a method for preparing cells for treating patients afflicted with CFS, which includes subjecting cells derived from lymph nodes excised from patients afflicted with CFS to mitogenic stimulation in serum-free media for their expansion. The resulting therapeutic agent for treating patients afflicted with CFS includes in a pharmaceutically-acceptable carrier, cytokine-producing cells having been produced by the step of subjecting cytokine-producing cells derived from lymph nodes excised from patients afflicted with CFS to mitogenic stimulation in serum-free media for their expansion.

As another aspect of the present invention, disclosed is a method for treating patients afflicted with CFS that includes administering to the patient an effective amount of the therapeutic agent disclosed herein. The invention also is capable of treating individuals afflicted with fibromyalgia syndrome ("FMS").

Finally, the invention further is effective in lowering activated T cell count in individuals where an activated T cell count is inappropriate (an immunologic abnormality), such as, for example, in CFS patients. See, for example, Cannon, et al., "Interleukin-1 beta, interleukin-1 receptor antagonist, and soluble interleukin-1 receptor type II secretion in chronic fatigue syndrome", *J Clin Immunol*, 1997 May; 17(3): 253–61; and Hassan, et al., "A study of the immunology of the chronic fatigue syndrome: correlation of immunologic parameters to health dysfunction", Clin Immunol Immunopathol, 1998 Apr, 87(1): 60–7. Such lowering of activated T cell count would appear to be a response evoked by the course of treatment disclosed herein for other disease conditions as well as CFS.

Advantages of the present invention include a culture procedure that is easy, expedient, and reproducible. Another advantage is a therapeutic agent that moderates many of the debilitating symptoms associated with CFS. A further advantage is that total lack of adverse side effects when using the novel therapeutic agent. These and other advantages will be readily apparent to those skilled in the art.

Figure 1:
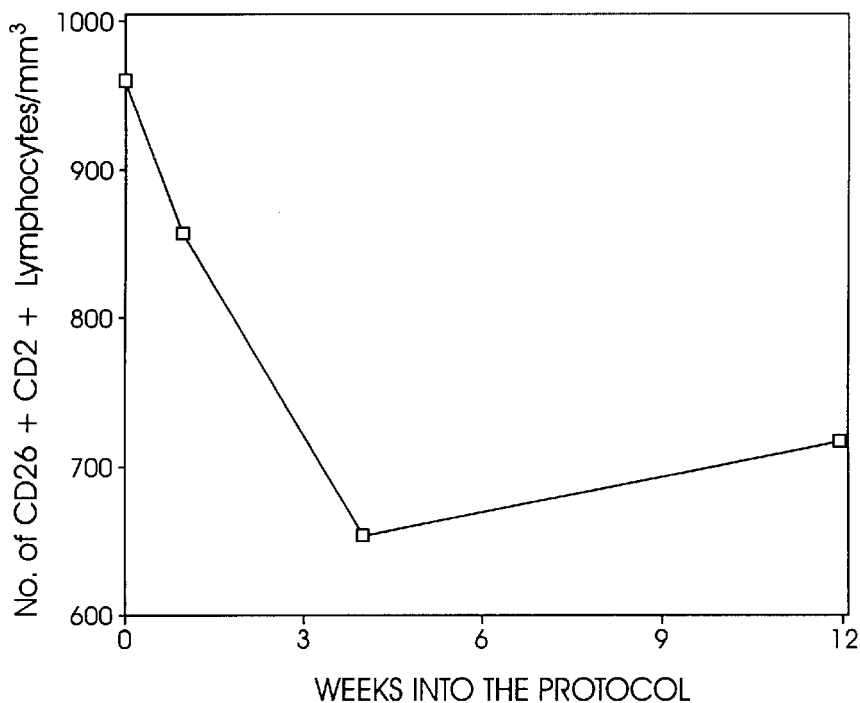
FIG. 1 graphically depicts for Patient 401 the effect of the inventive therapy on peripheral blood phenotype lymphocyte activation marker CD26 by plotting the number of CD26+CD4+ lymphocyte cells per mm$^3$ versus time following the therapy treatment.

The drawings will be described further in the Examples that follow.

DETAILED DESCRIPTION OF THE INVENTION

Cellular immunotherapy has been proposed to treat cancer in human patients (U.S. Pat. No. 5,814,295), leukemia in cats (U.S. Pat. No. 5,705,162), and human immunodeficiency virus (International Publication No. WO 97/30590). These proposals, however, all treat disease states associated with a virus that is responsible for the malady of the patient. In CFS and FMS (often, only CFS will be referred to herein for convenience, it being recognized that both CFS and FMS are meant), however, no causative agent, much less a virus, has been identified as being responsible for the disease state of the patient. Despite this lack of knowledge, the present invention has been found to be remarkably efficacious in treating patients afflicted with CFS. Since a compromised immune system results from cancer, FeLV, and HIV, cellular immunotherapy infuses cells that secrete cytokines and other agents that appear to treat the disease. In fact, International Publication No. WO 97/30590 even reports that some immune function was restored in some of the patients treated.

Now, the art reports on immune function and health of CFS patients since abnormal immune function (dysfunction) is associated with the disease. The inventive cellular immunotherapy reveals cells recovered from patient lymph nodes that have different immune profiles. The patients treated with such inventive cellular immunotherapy also respond somewhat differently. Whether their different response is indicative of a need to establish certain cellular profile of the cells for infusion presently is unknown. Whether treating a compromised immune function of the CFS patients is important for their recovery also is unknown. What is known, however, is that CFS patients with disease terms as long as 10 years have responded remarkably to the inventive cellular immunotherapy. Thus, while the mechanism of action remains not fully understood, its ability to help patients afflicted with CFS is clear.

The initial step of the invention is the excision of a lymph node from the CFS patient. A generalized lymphadenopathy is performed to excise a lymph which may be, for example, cervical, axillary, or inguinal. Other possible node sites include occipital, postauricular, preauricular, submental, paraspinal, and epitrochlear nodes. Cell and tissue dissociation is accomplished conventionally, such as by centrifugation, in order to harvest the LNLs. The excised nodes then are subjected to mitogenic stimulation. Initiation of cell expansion includes the initial use of serum-free Macrophage SFM media (Gibco/BRL, Grand Island, NY),. Additionally, mitogenic stimulation most preferably is conducted using IL-2 and soluble anti-CD$_3$ cells that are simultaneously added (rather than sequential addition and the use of plate-bound anti-CD$_3$ cells, as in the art). Aliquots of fresh media and cytokine are periodically added to the culture during their growth. Culture conditions are optimized to maintain the viability of the APCs present in the lymph nodes. Cells were cultured in serum-free conditions using a media designed to maintain the viability of macrophages and dendritic cells, and not lymphocytes. Cells expanded in serum-free conditions are known to be potentially less toxic.

The present invention uses the capacity of anti-CD3 MAb to mimic the normal pathways of T-cell activation and the capacity of IL-2 to expand multiple T-cell sub-populations from lymph nodes. Cell growth conditions are maintained for about 10–12 days in accordance with a cell growth regimen that is outlined in the examples below. Importantly, the cells are weaned from IL-2 towards the end of their growth so that they are not dependent upon added IL-2 for their viability. This translates into an important feature of the present invention, which is that, no auxiliary IL-2 is required to be administered to the patient. The toxicity of IL-2, thus, is avoided by the precepts of the present invention. Ideally, the infusion of cells as a vehicle for modulating the cytokine system addresses many of the limitations inherent to the systemic cytokine therapy. Theoretically, cells could traffic to reservoirs of viral or other activity and specifically release a variety of cytokines in a regulated fashion that could mediate both antiviral and immunorestorative effects; although, CFS patients are known to have a dysregulated immune system rather than a compromised or inactive immune system such as HIV patients have. Cytokines also are unlikely to be secreted or act individually, but rather as a "cascade" involving other cytokines, and regulated, local, i.e., paracrine, release appears to be critical to optimal activity.

The following examples illustrate the present invention, but they should not be construed as limiting. All citations referred to herein are expressly incorporated herein by reference.

EXAMPLES

In this clinical study, CFS patients were enrolled in they met the CDC guidelines (Fukuda, et al., and the International CFS Study Group, "The Chronic Fatigue Syndrome: A comprehensive approach to its definition and study", supra) with a history of acute onset, Karnofsky score 80, and evidence of immune dysfunction (3 or more of the following):

Elevated TNFRI in serum (>1 SD above controls)

Elevated TNFRI in PHA stimulated blood culture (>1 SD above control values)

Elevated IL-5 in PHA stimulated blood culture (>1 DS above controls)

Lymphocyte activation (CD2+CD26+ cells >50% positive)

Low NK cytotoxicity (<205 NKCC).

Patients were to have palpable peripheral lymph nodes that were considered to be easily accessible/resectable under local anesthesia. Patients also were to have adequate organ function defined by the following criteria within 2 weeks prior to enrollment:

Absolute neutrophil count 1,000/mm$^3$

Hemoglobin 9.5 g/dL

Platelet count 75,000/mm$^3$

Creatinine 1.5 mg/dl

Bilirubin 1.5 mg/dl

SGOT 3 ×upper normal limit.

Patients were excluded with HIV, Hepatitis B, Hepatitis C, and other active infections which would exclude the diagnosis of CFS; encephalopathy or malignancy; serologic or clinical evidence of autoimmune disease; active alcohol or recreational drug use; current or recent (within the prior 4 weeks) use of potentially immunomodulating therapies (steroids, cytolytic therapies, gamma globulin, cytokines, cytokine inhibitors) or therapy for an acute infection. Patients also were excluded in they had undergone a splenectomy, had major psychiatric illness, dyspnea on significant exertion (if clinically indicated adequate pulmonary functions must be documented by an $FEV_1$, and a DLCO of 70% predicted for height and age); or having a history of congestive heart failure, symptoms of coronary artery disease, or serious cardiac arrhythmia.

After each eligible patient had been subjected to a physical assessment (history, physical examination, activities of daily living (ADL), Sickness Impact Profile (SIP), Quality of Life index (QOL), Karnofsky performance status rating) and psychiatric and cognitive evaluation (Beck Depression Inventory, Hamnilton Anxiety Scale, Mental State Examination Interview, Boston Naming Test), a serial of laboratory tests were run as follows: CBC (with differential count), liver panel (total bilirubin, ALT, AST, LDH, alkaline phosphatase and serum albumin), metabolic panel (Na, K, Cl, $CO_2$, glucose, BUN, creatinine, uric acid, protein status), PT, PTF, urinalysis, chest X-ray, ECG, pulmonary function (if clinically indicated), and baseline immunologic studies (immunophenotyping, NK cytotoxicity, mitogen induced proliferation and cytokine production. Skin testing also was performed for cellular hypersensitivity: tetanus, toxoid, streptococcus, mumps, and Candida antigens.

Lymph node procurement involved the removal of 1–4 cm$^3$ lymph node material which was analyzed for presence of malignancy or infection by standard histologic techniques. The remaining node material was placed in a sterile container with transport medium (RIGS Cellular Culture Medium, Gaithersburg, MD) and antibiotics gentamicin (Abbott Laboratories) and vancomycin (Eli Lilly and Company). Lymph node processing involved the removal of extraneous tissue, mincing into 2–mm pieces, and crushing with the butt end of a sterile syringe plunger. Large capsular fragments were removed by unit gravity sedimentation and suspended cells transferred to centrifuge tubes and centrifuged at 200 ×g for 6 minutes. The cells then were resuspended in fresh medium, enumerated, and the percent viability determined.

Cell expansion involved an initial concentration of $10^6$/ml in medium (RIGS Cellular Culture Medium supplemented with 600 IU/ml of human recombinant IL-2 (Proleukin, Chiron Therapeutics, Emeryville, CA) and 10 ng/ml lanti-$CD_3$ (Orthoclone, OKT3, Ortho Pharmaceutical Corporation, Raritan, NY) in sterile culture bags (ETHOX, Buffalo, NY) and incubated at 37° C. in 5% $CO_2$ for 4 days. After 4 days, the cells were enumerated and percent viability determined. The cells then were resuspended in medium with 600 IU/ml or rIL-2 at $2.5 \times 10^5$ cells/ml density and returned to the incubator. At seven days, cell enumeration and viability evaluation was repeated and the cells then resuspended in medium containing 120 IU/ml rIL-2 at $3.5 \times 10^5$ cells/ml density and returned to the incubator. The maximum expansion was found to be achieved between 10–12 days of ex-vivo culture. Culture bags were observed daily for changes in medium color, cell density or abnormalities that could precipitate variance from cell expansion protocol.

At 10–12 days expansion, the cells were harvested and suspended in normal saline and human albumin for infusion. The following parameters were determined on cell end product or cell suspension prior to harvest:

Cell number and viability: a minimum 2-fold increase in cell number from isolated cell number with a minimum of 85% viability Endoxin assay: undetectable or <0.03 EU/ml Morphology of cytocentrifuge preparations: lymphocytic cells 85%

Gram stain: undetectable microorganisms

Cultures for aerobic and anaerobic bacteria and fungal contamination: cell culture will be tested 48 hours prior to cell harvest, criteria are negative grown for bacteria or fungal growth Determinations of lymphocyte subgroups and surface markers will be performed by 3 or 4 color flow cytometry with MAb versus the following: CD3, CD4, CD8, CD11b, CD25, CD 28, CD45RA, CD45RO, CD56, CD62L, CD95, HLA-DR, CD38, and inclusion criteria 85% CD3.

Cells were infused into the patients through an intravenous catheter over an approximately 10 to 30 minute time period (as fast as possible). Prior to infusion and at defined intervals thereafter, the patients were subjected to assessment in order to determine the effect of the treatment on CFS.

The following physical assessment, and psychiatric and cognitive evaluations, are reported for each patient:

| Test | Reference |
|---|---|
| Activity of Daily Living ↑ | |
| Quality of Life ↑ | |
| Karnofsky Score ↑ | Karnofsky, et al., "The Use of the nitrogen mustards in the palliative treatment of carcinoma", Cancer, 1948; 1: 634–652 |
| Beck Depression Scale ↓ | Beck, et al., "An inventory for measuring depression", Archives of General Psychiatry, 1981; 5: 561–571 |
| Hamilton Anxiety Scale ↓ | Weingarter, "Autonomic and effort-demanding cognitive processes in depression", |
| Mini Mental ↑ | |
| Trail Making A ↓ | Reitan Neuropsychology Laboratory, Tucson, AZ (originally part of the Army Individual Test Battery, 1944) |
| Trail Making B ↓ | Reitan Neuropsychology Laboratory, Tucson, AZ (originally part of the Army Individual Test Battery, 1944) |
| Word Fluency ↑ | Neurosensory Center for Comprehensive Examination for APHASIA (NCCEA) distributed by the Neuropsychology Laboratory of the University of Victoia |
| Symptom Impact Profile ↓ | Bergmer, et al., "The Sicikness Impact Profile: Development and final revision of a health status measure, Medical Care, 1981: 19(8): 787–807 |

PATIENT 401

This patient has had CFS for over 10 years with little waxing and waning of symptoms. He received $1.248 \times 10^9$ cells, which analyzed as follows:

| | | |
|---|---|---|
| 97% | CD3 | |
| 2% | CD19 | |
| 59% | CD8+62L+RA− | (memory cell, homes to lymph node) |
| 11% | CD8+62L−RA− | (memory cell, homes to gut) |
| 66% | CD8+CD38+ | (cytotoxic CD8) |
| 10% | CD8+CD38− | (CD8 cell expressing antiviral cytokines) |
| 7% | CD4RO+RA− | (memory CD4 cells) |
| 1% | CD4RO−RA+ | (naïve CD4 cells) |
| 67% | CD8RO+Ra− | (memory CD8 cells) |
| 5% | CD8RO−RA− | (naïve CD8 cells) |
| 91% | CD2+CD26+ | (activation marker, T cells) |
| 56% | CD8+Cd95+ | (CD8 cells expressing a marker of early apoptosis) |

Clinical markers of this patient were recorded before cell infusion (baseline, BL, repeated on two occasions) and at various time intervals following infusion. The results recorded for this patient are set forth below:

| Patient 401 Clinical Markers* | BL1 | BL2 | WK1 | WK4 | WK12 |
|---|---|---|---|---|---|
| Activity of Daily Living ↑ | 32 | 31 | 29 | 30 | 32 |
| Quality of Life ↑ | 83 | 98 | 96 | 86 | 103 |
| Karnofsky Score ↑ | 75 | 75 | 70 | 70 | 80 |
| Beck Depression Scale ↓ | 2 | 3 | 3 | 5 | 5 |
| Hamilton Anxiety Scale ↓ | 13 | 9 | 8 | 7 | 4 |
| Mini Mental ↑ | 29 | 28 | 30 | 30 | 30 |
| Trail Making A ↓ | 77.0 | 37.6 | 20.68 | 21.62 | 27.16 |
| Trail Making B ↓ | 99.0 | 52.3 | 40.06 | 78.0 | 44.28 |
| Word Fluency ↑ | 19 | 23 | 27 | 35 | 26 |
| Symptom Impact Profile ↓ | 22 | 10 | 13 | 21 | 7 |
| Sleep and Rest | 0 | 0 | 0 | 0 | 0 |
| Emotional Behavior | 1 | 0 | 1 | 2 | 0 |
| Body Care & Movement | 0 | 0 | 0 | 0 | 0 |
| Home Management | 1 | 1 | 2 | 2 | 0 |
| Mobility | 0 | 0 | 0 | 1 | 0 |
| Social Interactions | 7 | 2 | 2 | 6 | 2 |
| Ambulation | 0 | 0 | 1 | 1 | 0 |
| Alertness Behavior | 5 | 3 | 2 | 3 | 2 |
| Writing & Communication | 0 | 0 | 0 | 0 | 0 |
| Work Outside of Home | 4 | 2 | 2 | 3 | 1 |
| Recreation and Past Times | 4 | 2 | 3 | 3 | 2 |
| Eating | 0 | 0 | 0 | 0 | 0 |

*Interpretation:

| | |
|---|---|
| Activities of Daily Living | higher is better (35 is top of scale) |
| Sickness Impact Profile | lower is better |
| Quality of Life | higher is better |
| Karnofsky Score | higher is better |
| Beck Depression Inventory | lower is better |
| Hamilton Anxiety Scale | lower is better |
| Mini Mental (Folstein) | higher is better |
| Trail Making A and B | lower is better (seconds to complete task) |
| Word Fluency | higher is better |

In terms of importance, Trail Making A and B, and Word Fluency are discriminating tests while the Mini Mental test is not. Symptom Impact Profile is an import measure of CFS.

This patient verbally reported little improvement. His test scores, however, reveal that he responded clinically to the treatment: Symptom Impact Profile scores improved, particularly on the sub-scales of Social Interactions, Alertness Behavior, Working Outside of Home, and Recreation and Past Times. The baseline scores reveal the variability of the illness, and the caution that should be used in assigning causality to improvement. This patient's Quality of Life scores improved significantly, his Karnofsky marginally improved at Week 12, the Hamilton anxiety improved (though, he did not met anxiety criteria at any time period), and his Cognitive Assessment improved considerably as reflected in Trails A and B and Word Fluency scores.

Figure 2:
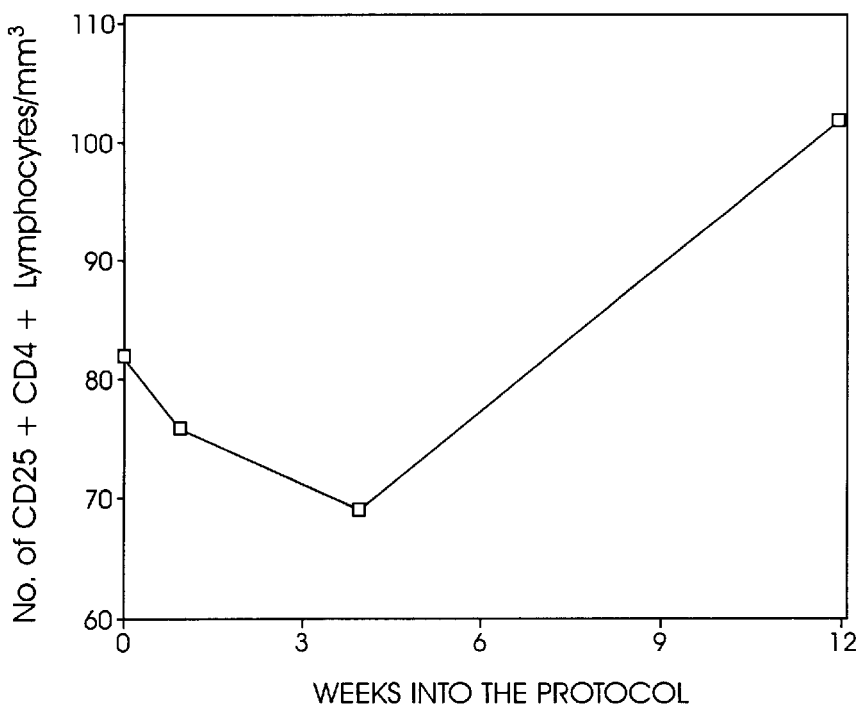
FIG. 2 graphically depicts for Patient 401 the effect of the inventive therapy on peripheral blood phenotype lymphocyte activation marker CD25 by plotting the number of CD25+CD4+ lymphocyte cells per mm$^3$ versus time following the therapy treatment.

Patient 401, like all of the other subjects reported, showed a marked reduction in the number of circulating activated T cells and activated CD8 cells. This reduction is shown graphically in FIG. 1. NK cell function did not change, but T cell function improved significantly (from a baseline stimulation index mean of 245 to a mean of 409 at weeks 1, 4, and 12). Plasma TNF-α and TNF-α receptor trended downward. PHA stimulated TNF-α and TNF-α receptor did not change. PHA stimulated IL-5 was reduced post therapy. This is displayed graphically in FIG. 2.

PATIENT 407

Clinically, this patient had been ill for approximately 5 years. A professional golfer, her illness has kept her off the circuit for the past 2 years; although, she is able to work part time. She received $5.2 \times 10^8$ cells, which analyzed as follows:

| | | |
|---|---|---|
| 95% | CD3 | |
| 5% | CD19 | |
| 48% | CD4 cells | (88% of these were memory, homes to lymph node) |
| 52% | CD8 cells | |
| 37% | CD8+62L+RA− | (memory cell, homes to lymph node) |
| 5% | CD8+62L−RA− | (memory cell, homes to gut) |
| 51% | CD8+CD38+ | (cytotoxic CD8) |
| 1% | CD8+CD38− | (CD8 cell expressing antiviral cytokines) |
| 45% | CD4RO+RA− | (memory CD4 cells) |
| 1% | CD4RO−RA+ | (naïve CD4 cells) |
| 38% | CD8RO+RA− | (memory CD8 cells) |
| 3% | CD8RO−RA− | (naïve CD8 cells) |
| 90% | CD2+CD26+ | (activation marker, T cells) |

Clinical markers of this patient were recorded before cell infusion (baseline, BL, repeated on two occasions) and at various time intervals following infusion. The results recorded for this patient are set forth below:

| Patient 407 Clinical Markers | BL1 | BL2 | WK1 | WK4 | WK12 |
|---|---|---|---|---|---|
| Activity of Daily Living ↑ | 26 | 26 | 26 | 27 | 31 |
| Quality of Life ↑ | 104 | 97 | 107 | 106 | 105 |
| Karnofsky Score ↑ | 75 | 75 | 70 | 70 | 70 |
| Beck Depression Scale ↓ | 10 | 7 | 8 | 5 | 4 |
| Hamilton Anxiety Scale ↓ | 2 | 2 | 3 | 4 | 2 |
| Mini Mental ↑ | 30 | 30 | 30 | 30 | 30 |
| Trail Making A ↓ | 25.8 | 19.44 | 24.37 | 21.82 | 15.62 |
| Trail Making B ↓ | 60.04 | 39.0 | 52.38 | 40.75 | 33.31 |
| Word Fluency ↑ | 22 | 39 | 37 | 45 | 45 |
| Symptom Impact Profile ↓ | 18 | 15 | 14 | 16 | 9 |
|   Sleep and Rest | 2 | 3 | 1 | 3 | 1 |
|   Emotional Behavior | 0 | 0 | 0 | 0 | 0 |
|   Body Care & Movement | 0 | 0 | 0 | 0 | 0 |
|   Home Management | 2 | 2 | 3 | 2 | 1 |
|   Mobility | 1 | 0 | 1 | 2 | 0 |
|   Social Interactions | 2 | 2 | 2 | 1 | 1 |
|   Ambulation | 2 | 1 | 1 | 2 | 0 |
|   Alertness Behavior | 3 | 1 | 1 | 1 | 0 |
|   Writing & Communication | 0 | 0 | 0 | 0 | 0 |
|   Work Outside of Home | 0 | 1 | 1 | 0 | 1 |
|   Recreation and Past Times | 5 | 4 | 4 | 4 | 4 |
|   Eating | 1 | 1 | 1 | 1 | 1 |

This subject verbally reported a modest improvement at week 1 with little further improvement. Her test scores, however, exhibit some evidence of clinical response, particularly in cognitive function. Her Sickness Impact Profile scores improved significantly, particularly on the sub-scales: Sleep and Rest, Social Interactions, Alertness Behavior. Her Activities of Daily Living scores improved, as did her Quality of Life and Beck Depression Inventory. Her Karnofsky Score decreased marginally (somewhat odd given the general improvement of her other scores) and her cognitive assessment improved considerably, as reflected in Trails A and B, and Word Fluency scores. Thus, clinically, she is considered a responder to the therapy.

Figure 3:
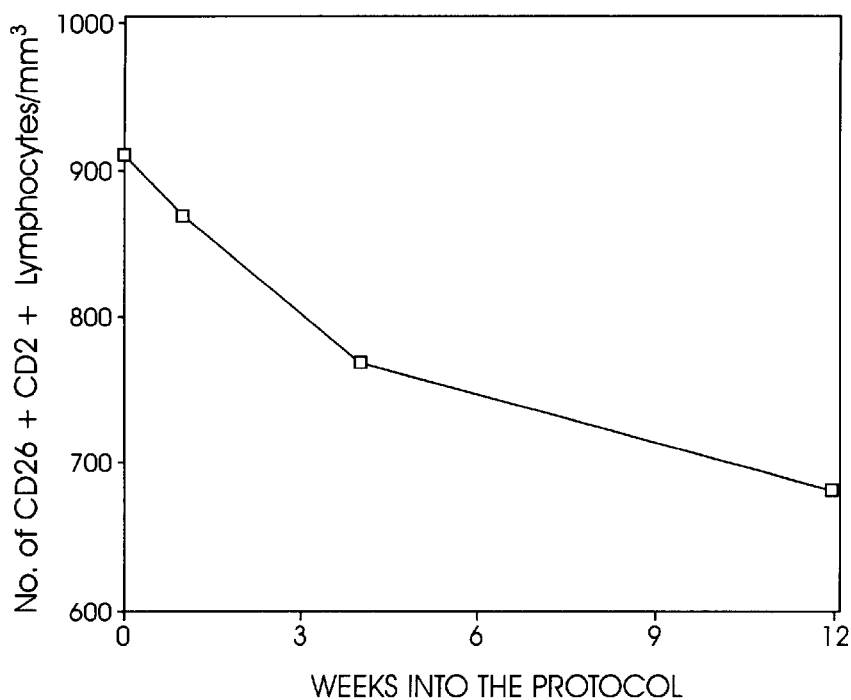
FIG. 3 graphically depicts for Patient 407 the effect of the inventive therapy on peripheral blood phenotype lymphocyte activation marker CD26 by plotting the number of CD26+CD4+ lymphocyte cells per mm$^3$ versus time following the therapy treatment, FIG. 4 graphically depicts for Patient 407 the effect of the inventive therapy on peripheral blood phenotype lymphocyte activation marker CD25 by plotting the number of CD25+CD4+ lymphocyte cells per mm$^3$ versus time following the therapy treatment.
Figure 4:
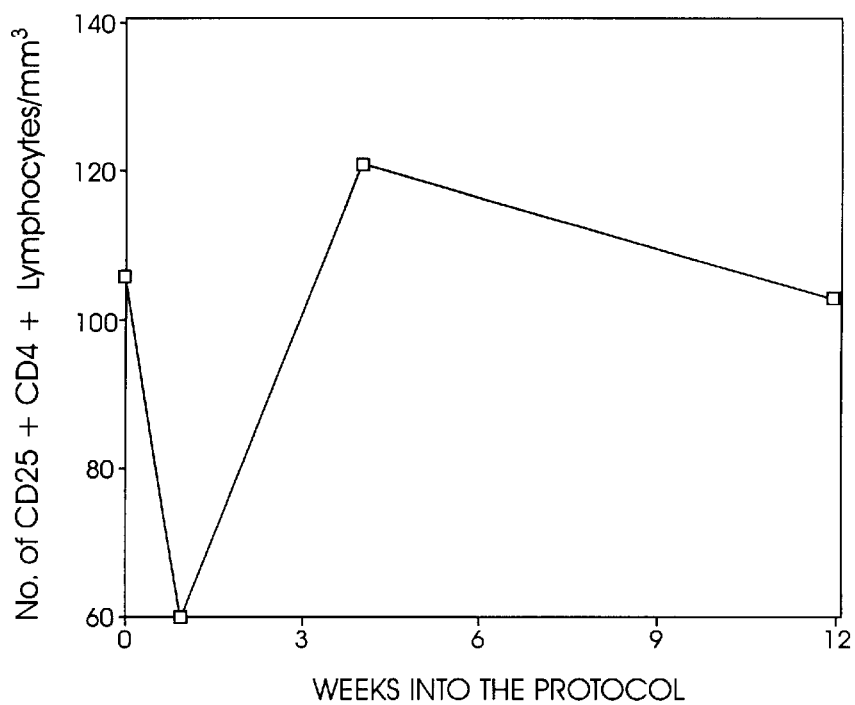

Patient 407, like the other patients, showed a marked reduction in the number of circulating activated T cells and activated CD8 cells. FIGS. 3 and 4 display this reduction. NK cell function improved, while T cell function did not improve. Plasma TNF-α initially increased, and TNF-α receptor was unchanged. PHA stimulated TNF-α was reduced. PHA stimulated IL-5 was reduced post therapy.

PATIENT 409

This patient had been ill with CFS for over 10 years. The course of her disease was variable and she has been predominantly housebound. Her illness also meets the clinical criteria of fibromyalgia. She received $8.63 \times 10^8$ cells, which analyzed as follows:

| | | |
|---|---|---|
| 96% | CD3 | |
| 4% | CD19 | |
| 46% | CD4 cells | (92% of these were memory, homes to lymph node) |
| 54% | CD8 cells | |
| 44% | CD8+62L+RA− | (memory cell, homes to lymph node) |
| 52% | CD8+62L−RA− | (memory cell, homes to gut) |
| 3% | CD8+CD38+ | (cytotoxic CD8) |
| 52% | CD8+CD38− | (CD8 cell expressing antiviral cytokines) |
| 39% | CD4RO+RA− | (memory CD4 cells) |
| 2% | CD4RO−RA+ | (naïve CD4 cells) |
| 41% | CD8RO+RA− | (memory CD8 cells) |
| 5% | CD8RO−RA− | (naïve CD8 cells) |
| 90% | CD2+CD26+ | (activation marker, T cells) |

Clinical markers of this patient were recorded before cell infusion (baseline, BL, repeated on two occasions) and at various time intervals following infusion. The results recorded for this patient are set forth below:

| Patient 409 Clinical Markers | BL1 | BL2 | WK1 | WK4 | WK12 |
|---|---|---|---|---|---|
| Activity of Daily Living ↑ | 23 | 23 | ND | 24 | 26 |
| Quality of Life ↑ | 81 | 87 | ND | 107 | 102 |
| Karnofsky Score ↑ | 75 | 75 | 80 | 85 | 80 |
| Beck Depression Scale ↓ | 7 | 8 | ND | 0 | 5 |
| Hamilton Anxiety Scale ↓ | 3 | 2 | 3 | 2 | 5 |
| Mini Mental ↑ | 30 | 30 | 30 | 27 | 30 |
| Trail Making A ↓ | 33.38 | 33.93 | 28.21 | 23.66 | 30.07 |
| Trail Making B ↓ | 75.0 | 60.0 | 57.28 | 53.31 | 54.47 |
| Word Fluency ↑ | 69 | 60 | 69 | 88 | 76 |
| Symptom Impact Profile ↓ | 25 | 55 | ND | 19 | 31 |
|   Sleep and Rest | 4 | 2 | ND | 0 | 2 |
|   Emotional Behavior | 0 | 1 | ND | 1 | 1 |
|   Body Care & Movement | 0 | 0 | ND | 0 | 1 |
|   Home Management | 5 | 3 | ND | 1 | 5 |
|   Mobility | 1 | 2 | ND | 1 | 3 |
|   Social Interactions | 6 | 7 | ND | 6 | 6 |
|   Ambulation | 0 | 3 | ND | 3 | 4 |
|   Alertness Behavior | 2 | 0 | ND | 1 | 2 |
|   Writing & Communication | 0 | 0 | ND | 0 | 0 |
|   Work Outside of Home | 0 | 0 | ND | 0 | 0 |
|   Recreation and Past Times | 6 | 3 | ND | 6 | 6 |
|   Eating | 1 | 1 | ND | 0 | 1 |

This subject, who verbally reported marked improvement, claimed that she felt "100%" at week one, but felt that she maintained at least a 50% improvement overall at week 12. Unfortunately, she felt well enough to undergo an extensive dental revision, with a dozen oral surgeries, and has had a series of adverse reactions to the lidocaine. Therefore, her Week 12 scores (taken 2 days after an oral surgery), pick up on these adverse reactions.

Her Sickness Impact Profile scores improved significantly at Week 4, particularly on the subscales: Sleep and Rest, and Home Improvement. Her Activities of Daily Living scores improved, Quality of Life scores improved, Beck Depression Inventory improved, here Karnofsky Score improved, and her cognitive assessment considerably, as reflected in Trails A and B, and Word Fluency scores. She definitely responded to this therapy.

Figure 5:
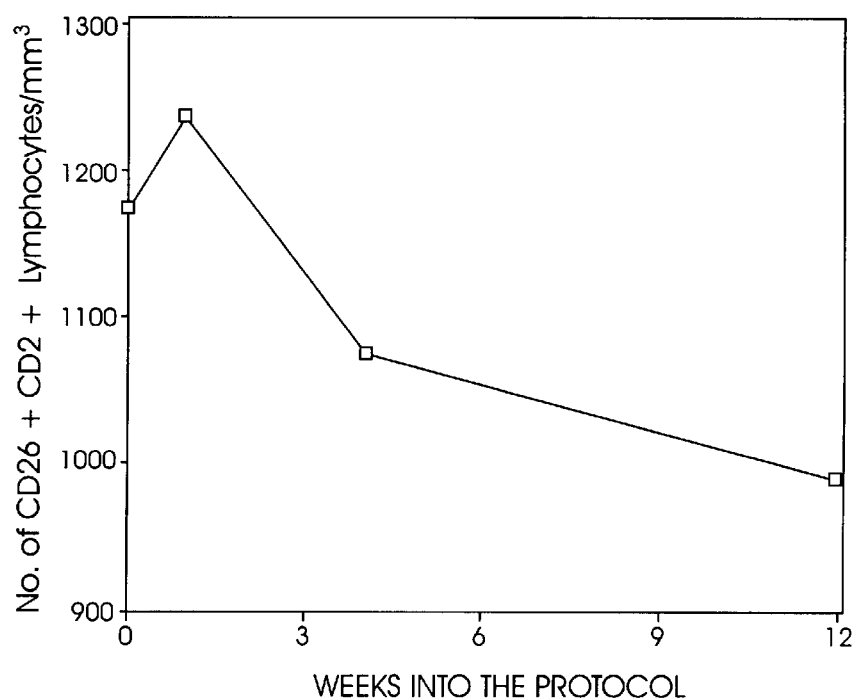
FIG. 5 graphically depicts for Patient 409 the effect of the inventive therapy on peripheral blood phenotype lymphocyte activation marker CD26 by plotting the number of CD26+CD4+ lymphocyte cells per mm$^3$ versus time following the therapy treatment.
Figure 6:
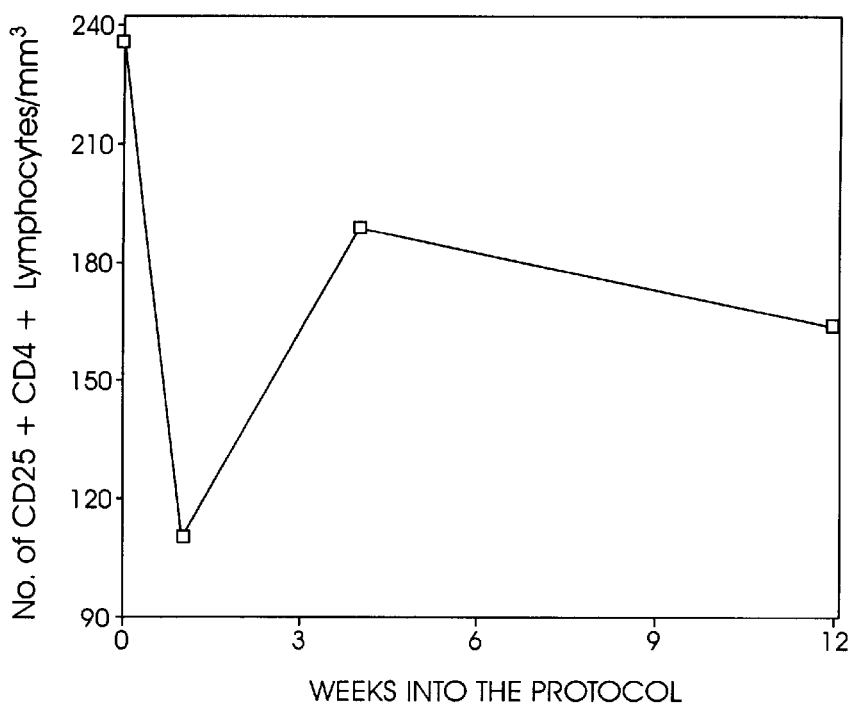
FIG. 6 graphically depicts for Patient 409 the effect of the inventive therapy on peripheral blood phenotype lymphocyte activation marker CD25 by plotting the number of CD25+CD4+lymphocyte cells per mm$^3$ versus time following the therapy treatment.

Patient 409, like all of the other patients, showed a marked reduction in the number of circulating activated T cells, and activated CD8 cells. FIGS. 5 and 6 show this reduction. NK cell function improved, as did T cell function. Plasma TNF-α initially increased, and TNF-α receptor was unchanged. PHA stimulated IL-5 was reduced post-therapy.

PATIENT 411

Clinically, this patient has had greater than 10 years of CFS illness, variable course, and was predominantly housebound. Her illness also meets the clinical criteria for fibromyalgia. She was given $6.336 \times 10^9$ cells, which analyzed as follows:

| | | |
|---|---|---|
| 98% | CD3 | |
| 2% | CD19 | |
| 28% | CD4 cells | (92% of these were memory, homes to lymph node) |
| 77% | CD8 cells | |
| 68% | CD8+62L+RA− | (memory cell, homes to lymph node) |
| 3% | CD8+62L−RA− | (memory cell, homes to gut) |
| 5% | CD8+CD38+ | (cytotoxic CD8) |
| 74% | CD8+CD38− | (CD8 cell expressing antiviral cytokines) |
| 26% | CD4RO+RA− | (memory CD4 cells) |
| 2% | CD4RO−RA+ | (naïve CD4 cells) |
| 67% | CD8RO+RA− | (memory CD8 cells) |
| 6% | CD8RO−RA− | (naïve CD8 cells) |
| 95% | CD2+CD26+ | (activation marker, T cells) |

Note, that this patient has a very different pattern of expression of CD38 cells (74%) than did the other patients. The significance of the different pattern of expression is not yet fully known.

Clinical markers of this patient were recorded before cell infusion (baseline, BL, repeated on two occasions) and at various time intervals following infusion. The results recorded for this patient are set forth below:

| Patient 411 Clinical Markers | BL1 | BL2 | WK1 | WK4 | WK12 |
|---|---|---|---|---|---|
| Activity of Daily Living ↑ | 24 | 24 | 27 | 27 | 26 |
| Quality of Life ↑ | 56 | 66 | 88 | 93 | 77 |
| Karnofsky Score ↑ | 70 | 70 | 80 | 85 | 80 |
| Beck Depression Scale ↓ | 24 | 25 | 11 | 13 | 18 |
| Hamilton Anxiety Scale ↓ | 24 | 24 | 11 | 7 | 9 |
| Mini Mental ↑ | 30 | 30 | 30 | 30 | 30 |
| Trail Making A ↓ | 35.53 | 27.63 | 16.93 | 15.21 | 20.15 |
| Trail Making B ↓ | 81.59 | 76.66 | 66.41 | 55.53 | 58.19 |
| Word Fluency ↑ | 35 | 36 | 46 | 40 | 46 |
| Symptom Impact Profile ↓ | 55 | 63 | 43 | 29 | 48 |
|   Sleep and Rest | 2 | 5 | 3 | 1 | 2 |
|   Emotional Behavior | 6 | 2 | 1 | 0 | 2 |
|   Body Care & Movement | 7 | 7 | 6 | 3 | 6 |
|   Home Management | 5 | 9 | 5 | 4 | 5 |
|   Mobility | 5 | 6 | 3 | 4 | 4 |
|   Social Interactions | 12 | 12 | 9 | 8 | 10 |
|   Ambulation | 4 | 6 | 4 | 2 | 3 |
|   Alertness Behavior | 9 | 10 | 8 | 5 | 9 |
|   Writing & Communication | 2 | 2 | 1 | 0 | 2 |
|   Work Outside of Home | 0 | 0 | 0 | 0 | 0 |
|   Recreation and Past Times | 2 | 3 | 2 | 2 | 4 |
|   Eating | 1 | 1 | 1 | 0 | 1 |

This subject verbally reported marked improvement in her condition. Her Sickness Impact Profile scores improved significantly at Week 4, particularly on the sub-scales: Sleep and Rest, and Home Improvement. Her Activities of Daily Living scores improved as did her Quality of Life scores, Beck Depression Inventory, and Karnofsky Scores. Her Cognitive assessment improved considerably, as reflected in Trails A and B, and Word Fluency scores. She definitely responded to the therapy.

Figure 7:
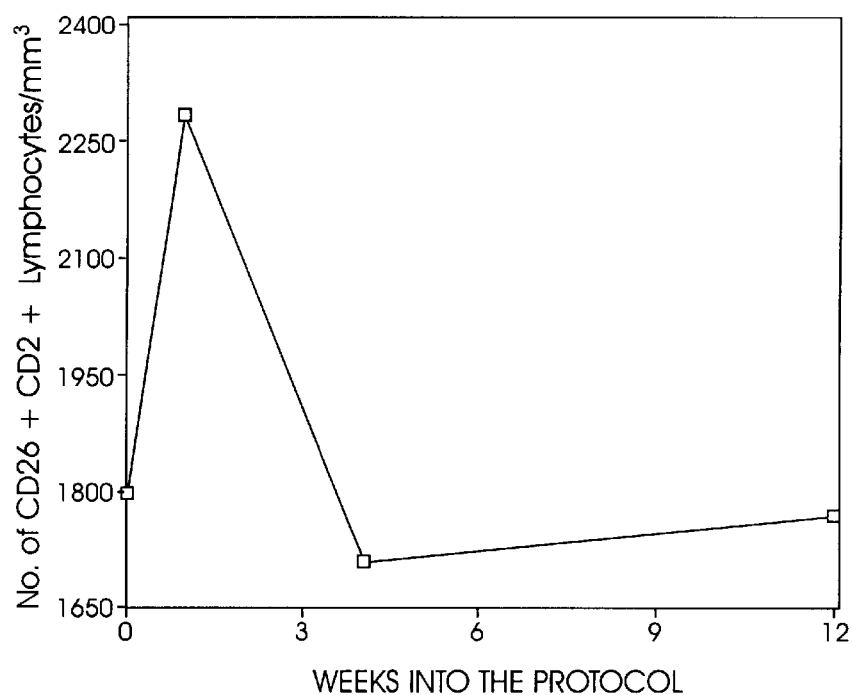
FIG. 7 graphically depicts for Patient 411 the effect of the inventive therapy on peripheral blood phenotype lymphocyte activation marker CD26 by plotting the number of CD26+CD4+ lymphocyte cells per mm$^3$ versus time following the therapy treatment.
Figure 8:
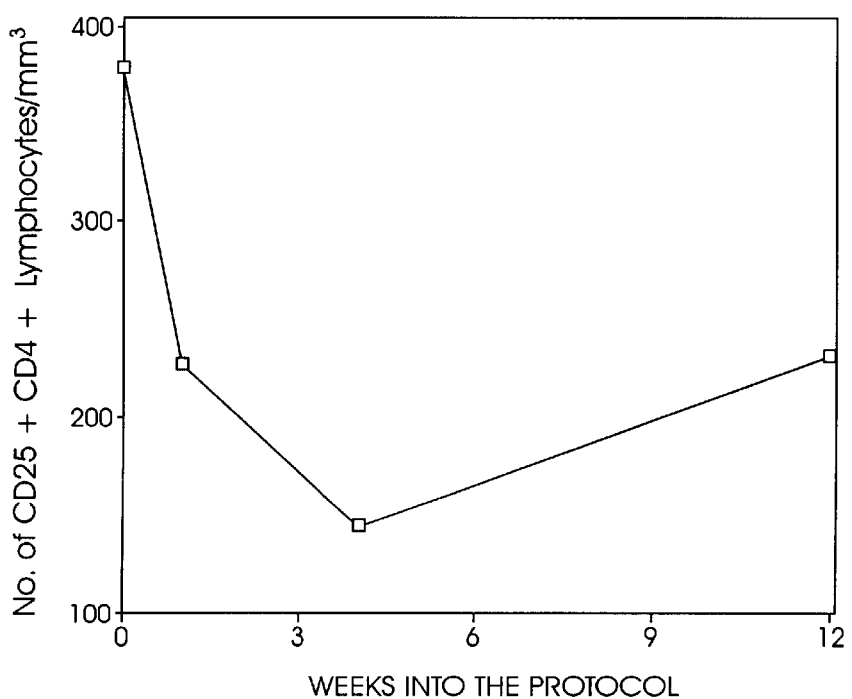
FIG. 8 graphically depicts for Patient 411 the effect of the inventive therapy on peripheral blood phenotype lymphocyte activation marker CD25 by plotting the number of CD25+CD4+ lymphocyte cells per mm$^3$ versus time following the therapy treatment.

Patient 411, like all of the other patients, showed a marked reduction in the number of circulating activated T cells, and activated CD8 cells. FIGS. 7 and 8 show this reduction. NK cell function improved, as did T cell function. Plasma TNF-α initially increased, and TNF-α receptor was unchanged. PHA stimulated IL-5 was reduced post-therapy.

PATIENT 412

Clinically, this patient has had greater than 10 years of CFS illness, variable course, and was predominantly housebound. Her illness also meets the clinical criteria for fibromyalgia. She was given $346 \times 10^8$ cells, which analyzed as follows:

| | | |
|---|---|---|
| 94% | CD3 | |
| 3% | CD19 | |
| 39% | CD4 cells | (92% of these were memory, homes to lymph node) |
| 57% | CD8 cells | |
| 41% | CD8+62L+RA− | (memory cell, homes to lymph node) |
| 12% | CD8+62L−RA− | (memory cell, homes to gut) |
| 19% | CD8+CD38+ | (cytotoxic CD8) |
| 38% | CD8+CD38− | (CD8 cell expressing antiviral cytokines) |
| 35% | CD4RO+RA− | (memory CD4 cells) |
| 3% | CD4RO−RA+ | (naïve CD4 cells) |
| 29% | CD8RO+RA− | (memory CD8 cells) |
| 23% | CD8RO−RA− | (naïve CD8 cells) |
| 93% | CD2+CD26+ | (activation marker, T cells) |

Yet another pattern of expression of CD38 cells is evident for this patient with more than Patients 401 and 407, but less than Patients 411 and 412. This patient also evidenced more naïve cells and more cells that home to the gut.

Clinical markers of this patient were recorded before cell infusion (baseline, BL, repeated on two occasions) and at various time intervals following infusion. The results recorded for this patient are set forth below:

| Patient 412 Clinical Markers | BL1 | BL2 | WK1 | WK4 | WK12 |
|---|---|---|---|---|---|
| Activity of Daily Living ↑ | 28 | 27 | 26 | 26 | — |
| Quality of Life ↑ | 100 | 90 | 91 | 92 | — |
| Karnofsky Score ↑ | 75 | 75 | 75 | 75 | — |
| Beck Depression Scale ↓ | 9 | 8 | 9 | 13 | — |
| Hamilton Anxiety Scale ↓ | 2 | 2 | 4 | 6 | — |
| Mini Mental ↑ | 30 | 30 | 30 | 30 | — |
| Trail Making A ↓ | 24.43 | 26.19 | 22.63 | 28.88 | — |
| Trail Making B ↓ | 47.69 | 48.44 | 42.78 | 48.7 | — |
| Word Fluency ↑ | 52 | 51 | 51 | 48 | — |
| Symptom Impact Profile ↓ | 18 | 33 | 17 | 23 | — |
|   Sleep and Rest | 4 | 4 | 3 | 1 | — |
|   Emotional Behavior | 0 | 2 | 1 | 2 | — |
|   Body Care & Movement | 1 | 5 | 2 | 3 | — |
|   Home Management | 5 | 2 | 0 | 3 | — |
|   Mobility | 0 | 2 | 0 | 0 | — |
|   Social Interactions | 0 | 4 | 3 | 3 | — |
|   Ambulation | 4 | 3 | 4 | 5 | — |
|   Alertness Behavior | 2 | 6 | 2 | 4 | — |
|   Writing & Communication | 0 | 0 | 0 | 0 | — |
|   Work Outside of Home | 0 | 0 | 0 | 0 | — |
|   Recreation and Past Times | 1 | 5 | 2 | 2 | — |
|   Eating | 1 | 0 | 0 | 0 | — |

This subject verbally reported marked improvement in her condition. Her Sickness Impact Profile scores improved significantly at Week 4, on nearly all of the sub-scales. Her Activities of Daily Living scores improved as did her Quality of Life scores improve, Beck Depression Inventory improve, Anxiety Scale diminish, and Karnofsky Scores improve. Her Cognitive assessment improved considerably, as reflected in Trails A and B, and Word Fluency scores. She definitely responded to the therapy.

Figure 9:
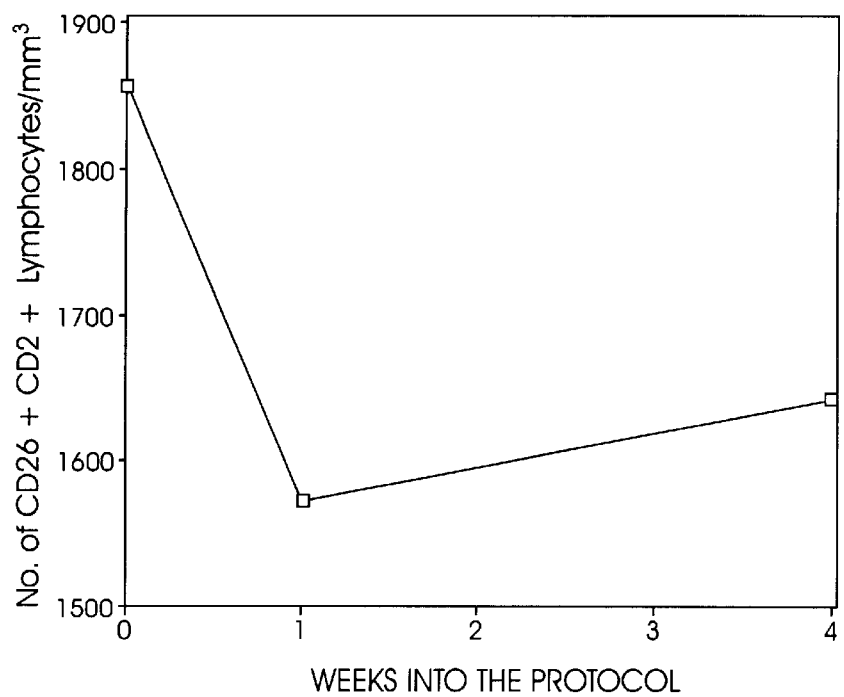
FIG. 9 graphically depicts for Patient 412 the effect of the inventive therapy on peripheral blood phenotype lymphocyte activation marker CD26 by plotting the number of CD26+CD4+ lymphocyte cells per mm$^3$ versus time following the therapy treatment.
Figure 10:
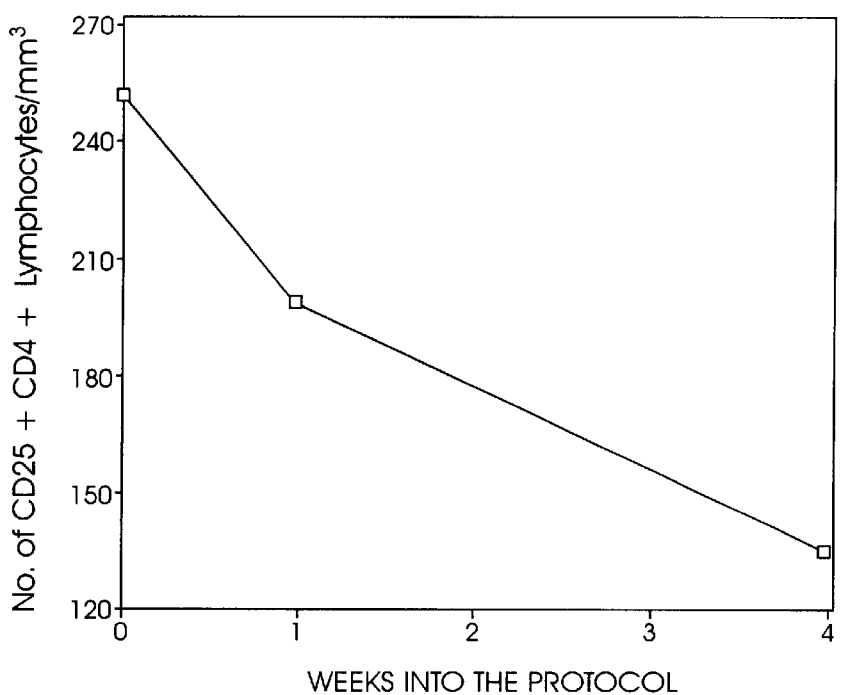
FIG. 10 graphically depicts for Patient 412 the effect of the inventive therapy on peripheral blood phenotype lymphocyte activation marker CD25 by plotting the number of CD25+CD4+ lymphocyte cells per mm$^3$ versus time following the therapy treatment.

Patient 412, like all of the other patients, showed a marked reduction in the number of circulating activated T cells, and activated CD8 cells. FIGS. 9 and 10 show this reduction. NK cell function improved, as did T cell function. Plasma TNF-α showed no change. PHA stimulated TNF-α increased, as did PHA stimulated IL-5.

PATIENT 413

Clinically, this patient has had greater than 10 years of CFS illness, variable course, and was predominantly housebound. Her illness also meets the clinical criteria for fibromyalgia. She was given $346 \times 10^8$ cells, which analyzed as follows:

| | | |
|---|---|---|
| 96% | CD3 | |
| 2% | CD19 | |
| 58% | CD4 cells | (92% of these were memory, homes to lymph node) |
| 38% | CD8 cells | |
| 2% | CD8+62L+RA− | (memory cell, homes to lymph node) |
| 0% | CD8+62L−RA− | (memory cell, homes to gut) |
| 37% | CD8+CD38+ | (cytotoxic CD8) |
| 1% | CD8+CD38− | (CD8 cell expressing antiviral cytokines) |
| 1% | CD4RO+RA− | (memory CD4 cells) |
| 0% | CD4RO−RA+ | (naïve CD4 cells) |
| 1% | CD8RO+RA− | (memory CD8 cells) |
| 0% | CD8RO−RA− | (naïve CD8 cells) |
| 95% | CD2+CD26+ | (activation marker, T cells) |

This patient exhibited a different pattern of expression of CD38 cells, somewhat like that of Patients 401 and 407. This patient also expressed many immature cells and double positive RO RA cells.

Clinical markers of this patient were recorded before cell infusion (baseline, BL, repeated on two occasions) and at various time intervals following infusion. The results recorded for this patient are set forth below:

| Patient 413 Clinical Markers | BL1 | BL2 | WK1 | WK4 | WK12 |
|---|---|---|---|---|---|
| Activity of Daily Living ↑ | 31 | 33 | 32 | 33 | — |
| Quality of Life ↑ | 89 | 97 | 99 | 107 | — |
| Karnofsky Score ↑ | 75 | 80 | 80 | 80 | — |
| Beck Depression Scale ↓ | 8 | 7 | 8 | 7 | — |
| Hamilton Anxiety Scale ↓ | 6 | 6 | 6 | 6 | — |
| Mini Mental ↑ | 28 | 26 | 30 | 29 | — |
| Trail Making A ↓ | 47.90 | 25.22 | 46.41 | 25.35 | — |
| Trail Making B ↓ | 62.12 | 77.53 | 60.87 | 88.19 | — |
| Word Fluency ↑ | 34 | 34 | 36 | 39 | — |
| Symptom Impact Profile ↓ | 25 | 20 | 19 | 19 | — |
|     Sleep and Rest | 3 | 3 | 2 | 2 | — |
|     Emotional Behavior | 1 | 2 | 2 | 2 | — |
|     Body Care & Movement | 0 | 2 | 0 | 2 | — |
|     Home Management | 1 | 2 | 3 | 1 | — |
|     Mobility | 8 | 3 | 4 | 6 | — |
|     Social Interactions | 0 | 0 | 1 | 0 | — |
|     Alertness Behavior | 6 | 4 | 4 | 3 | — |
|     Writing & Communication | 0 | 0 | 1 | 0 | — |
|     Work Outside of Home | 0 | 0 | 0 | 0 | — |
|     Recreation and Past Times | 3 | 3 | 1 | 2 | — |
|     Eating | 0 | 0 | 0 | 0 | — |

This subject verbally reported marked improvement. Her Sickness Impact Profile scores improved at Week 4, particularly on Alertness Behavior. Her Activities of Daily Living scores have not yet improved. Her Quality of Life Scores have improved, her Karnofsky Score has improved modestly, and unlike the other patients, her cognitive assessment has not improved, as reflected in Trails A and B, and Word Fluency scores. To date, this patient has not responded to the treatment.

Figure 11:
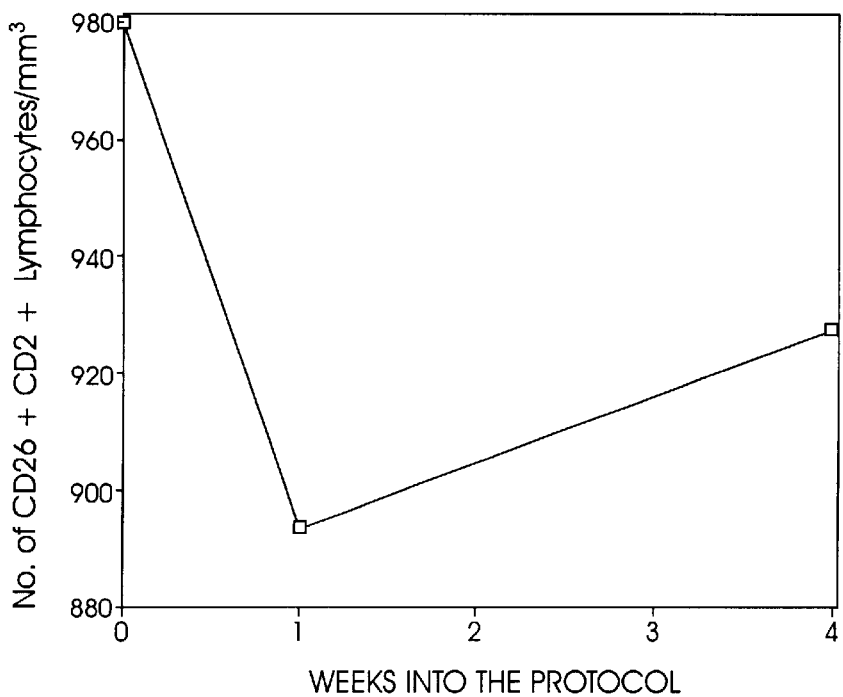
FIG. 11 graphically depicts for Patient 413 the effect of the inventive therapy on peripheral blood phenotype lymphocyte activation marker CD26 by plotting the number of CD26+CD4+ lymphocyte cells per mm$^3$ versus time following the therapy treatment.
Figure 12:
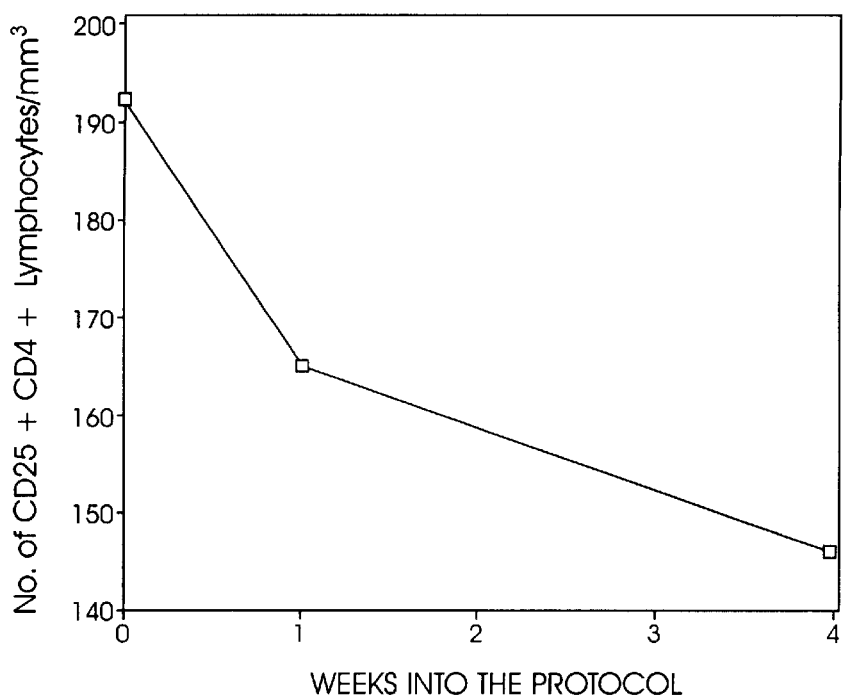
FIG. 12 graphically depicts for Patient 413 the effect of the inventive therapy on peripheral blood phenotype lymphocyte activation marker CD25 by plotting the number of CD25+CD4+ lymphocyte cells per mm$^3$ versus time following the therapy treatment.

Patient 413, like all of the other patients, showed a marked reduction in the number of circulating activated T cells, and activated CD8 cells. FIGS. 11 and 12 show this reduction. NK cell function improved, as did T cell function. Plasma TNF-α showed no change. PHA stimulated TNF-α increased, as did PHA stimulated IL-5.

I claim:

1. A therapeutic agent for treating patients afflicted with chronic fatigue syndrome (CFS), which comprises:

in a pharmaceutically-acceptable carrier, cytokine-producing cells having been produced by the step of subjecting cells derived from autologous lymph nodes excised from patients afflicted with CFS to mitogenic stimulation in serum-free media for their expansion.

2. The therapeutic agent of claim 1, wherein said anti-CD3 monoclonal antibody is present in an amount of between about 1 and 100 ng/ml and said IL-2 is present in an amount of about 600 IU/ml.

3. The therapeutic agent of claim 2, wherein the amount of IL-2 is lowered to about 120 IU/ml after 7 days of expansion.

4. The therapeutic agent of claim 3, wherein said expansion extends to at least about 10 days.

5. A method for treating patients afflicted with chronic fatigue syndrome (CFS), which comprises:

administering to said patient the autologous therapeutic agent of claim 1.

6. A method for treating patients afflicted with chronic fatigue syndrome (CFS), which comprises:

administering to said patient the autologous therapeutic agent of claim 2.

7. A method for treating patients afflicted with chronic fatigue syndrome (CFS), which comprises:

administering to said patient the autologous therapeutic agent of claim 3.

8. A method for treating patients afflicted with chronic fatigue syndrome (CFS), which comprises:

administering to said patient the autologous therapeutic agent of claim 4.

* * * * *